(12) United States Patent
Lombardo et al.

(10) Patent No.: US 9,349,516 B2
(45) Date of Patent: May 24, 2016

(54) MULTIDIRECTIONAL MAGNETIC PARTICLE INSPECTION SYSTEM

(71) Applicant: Siemens Energy, Inc., Orlando, FL (US)

(72) Inventors: Erik A. Lombardo, Sharon, SC (US); David S. Segletes, York, SC (US)

(73) Assignee: SIEMENS ENERGY, INC., Orlando, FL (US)

( * ) Notice: Subject to any disclaimer, the term of this patent is extended or adjusted under 35 U.S.C. 154(b) by 176 days.

(21) Appl. No.: 14/179,730

(22) Filed: Feb. 13, 2014

(65) Prior Publication Data

US 2015/0228392 A1    Aug. 13, 2015

(51) Int. Cl.
*G01N 27/82* (2006.01)
*H01F 13/00* (2006.01)
*G01N 27/84* (2006.01)

(52) U.S. Cl.
CPC .............. *H01F 13/003* (2013.01); *G01N 27/84* (2013.01)

(58) Field of Classification Search
CPC ..... G01N 27/82; G01N 27/902; G01N 27/72; G01N 27/83; G01N 27/84; G01N 2291/2693; H01F 13/003; H01F 13/00; G08B 13/2411; H02K 15/03; H02K 41/031; G03F 7/70758; G01R 33/00; G01R 33/12; G01R 33/0322; G01M 5/0091
USPC ......... 324/215, 216, 222, 228, 232, 234, 237, 324/238, 240, 241, 71.4, 245–263, 220, 324/221, 242, 243, 244.1, 456; 702/35; 228/103, 104; 356/237.1, 237.3, 239.7, 356/239, 239.8; 361/748–804
See application file for complete search history.

(56) References Cited

U.S. PATENT DOCUMENTS

| | | | |
|---|---|---|---|
| 3,855,530 A * | 12/1974 | Fuji ........................ | G01N 27/84 324/216 |
| 5,633,583 A | 5/1997 | Podney | |
| 6,040,695 A * | 3/2000 | Raulerson ............... | B82Y 15/00 324/240 |
| 7,948,349 B2 * | 5/2011 | Haratani ................ | G01R 33/09 324/249 |
| 8,314,611 B2 | 11/2012 | Viertl et al. | |
| 8,884,614 B2 * | 11/2014 | Wang .................... | G01R 33/028 324/228 |
| 2004/0178790 A1 * | 9/2004 | Gifford ................ | G01N 27/904 324/242 |
| 2004/0257072 A1 * | 12/2004 | Samson ............... | G01N 27/902 324/242 |
| 2006/0164080 A1 | 7/2006 | Popovic et al. | |
| 2010/0142753 A1 * | 6/2010 | Vetterlein ............... | G01N 27/84 382/100 |
| 2012/0074932 A1 * | 3/2012 | De Smet ........... | G01N 27/9046 324/240 |
| 2012/0293168 A1 | 11/2012 | Segletes et al. | |

FOREIGN PATENT DOCUMENTS

| | | | |
|---|---|---|---|
| FR | 2500931 | A1 | 9/1982 |
| GB | 2278449 | A | 11/1991 |
| WO | 9311428 | A1 | 6/1993 |

* cited by examiner

*Primary Examiner* — Arleen M Vazquez
*Assistant Examiner* — Steven Yeninas

(57) ABSTRACT

A magnetic particle inspection system for inspecting a plurality of articles. The system includes a first magnetizing coil for generating a first magnetic field oriented in a first direction. The system also includes a second magnetizing coil for generating a second magnetic field oriented in a second direction perpendicular to the first direction, wherein the first and second magnetizing coils are located in a common plane. In addition, the system may include a mat having a plurality of drainage holes, wherein the first and second magnetizing coils are located in the mat and the first and second magnetizing coils are sized to inspect a plurality of articles. Further, the system includes a power supply for supplying power for energizing the first and second magnetizing coils and a switching unit for switching current flow between the first and second magnetizing coils.

10 Claims, 4 Drawing Sheets

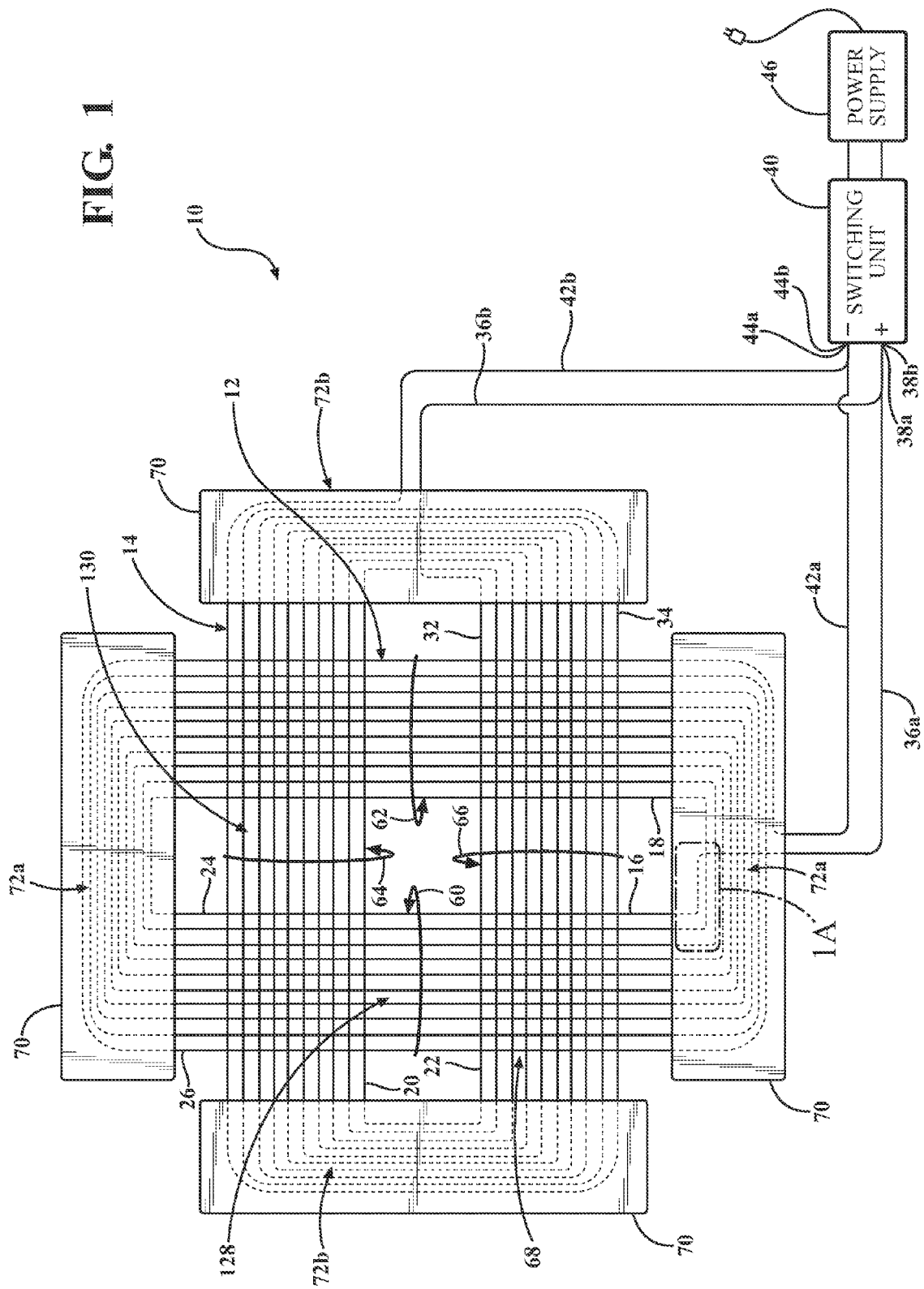

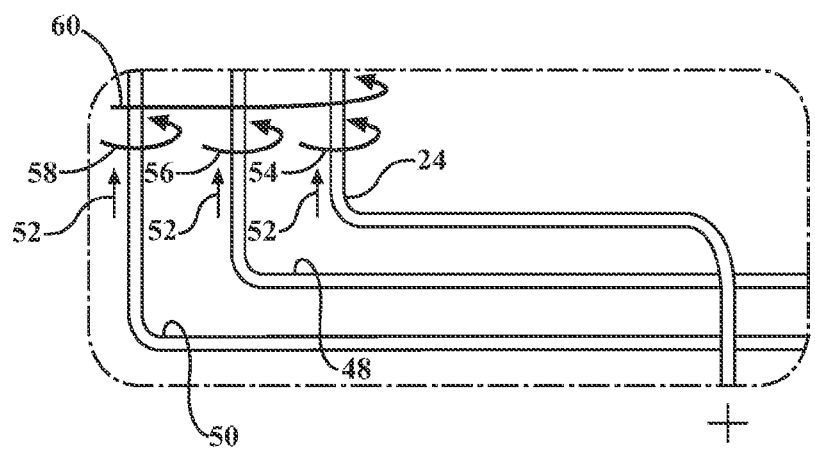
FIG. 1A
FIG. 2
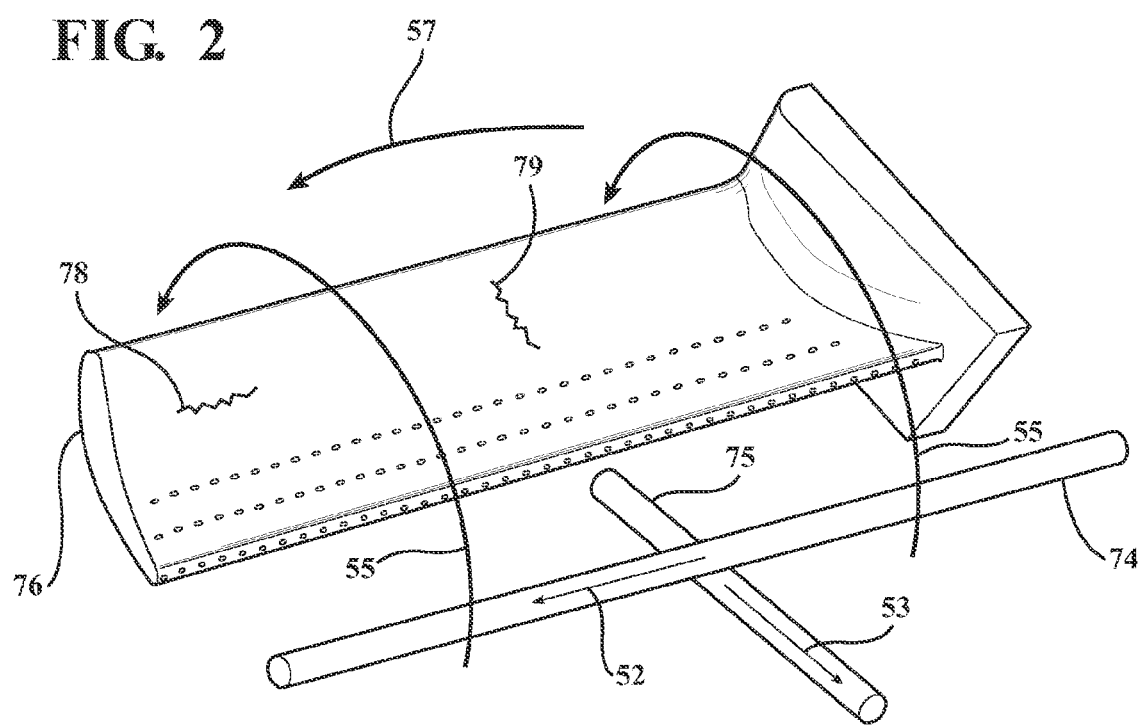

MULTIDIRECTIONAL MAGNETIC PARTICLE INSPECTION SYSTEM

FIELD OF THE INVENTION

This invention relates to magnetic particle inspection systems, and more particularly, to a system that includes a first magnetizing coil for generating a first magnetic field oriented in a first direction and a second magnetizing coil for generating a second magnetic field oriented in a second direction perpendicular to the first direction, wherein the first and second magnetizing coils are located in a common plane.

BACKGROUND OF THE INVENTION

Nondestructive (NDT) techniques are frequently used to evaluate manufacturing quality and integrity of mechanical components and structures. One such technique is magnetic particle inspection (MPI) which provides an indication of a flaw, such as irregularities or discontinuities, that may exist at or near the surface of a component, structure or other article fabricated from a ferromagnetic material. During an MPI, the article is subjected to a magnetic field generated by an outside source such as a coil or by passing an electric current through the article. The presence of a surface or near surface flaw causes a leakage in the magnetic field in the area of the flaw. Magnetic particles are applied to the article which are then attracted to the area of leakage in the magnetic field. The magnetic particles then accumulate in the area to form a flaw indication. The indication can then be used to evaluate manufacturing quality of the article.

MPI equipment used to generate the magnetic fields includes a bench unit that holds a single article during the inspection process. During use, the MPI equipment is configured so that the article is subjected to a magnetic field oriented in a first direction. The equipment configuration is then changed in order to provide a magnetic field oriented in a second direction perpendicular to the first direction to increase the likelihood of the detection of any flaw in the article. However, changing the equipment configuration is time consuming thus hindering productivity in a high volume production environment.

SUMMARY OF THE INVENTION

A magnetic particle inspection system for inspecting a plurality of articles is disclosed. The system includes a first magnetizing coil for generating a first magnetic field oriented in a first direction. The system also includes a second magnetizing coil for generating a second magnetic field oriented in a second direction perpendicular to the first direction, wherein the first and second magnetizing coils are located in a common plane. In addition, the system may include a mat having a plurality of drainage holes, wherein the first and second magnetizing coils are located in the mat and the first and second magnetizing coils are sized to inspect a plurality of articles. Further, the system includes a power supply for supplying power for energizing the first and second magnetizing coils and a switching unit for switching current flow between the first and second magnetizing coils.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

FIG. 1 depicts a multidirectional magnetic particle inspection system in accordance with the invention.

FIG. 1A is an exemplary partial view of a first leg of a first coil that depicts a first innermost turn and subsequent second and third turns of the first coil.

FIG. 2 is an exemplary view of a turn of the first coil located underneath a turbine blade of a gas turbine.

DETAILED DESCRIPTION OF THE INVENTION

Figure 3:
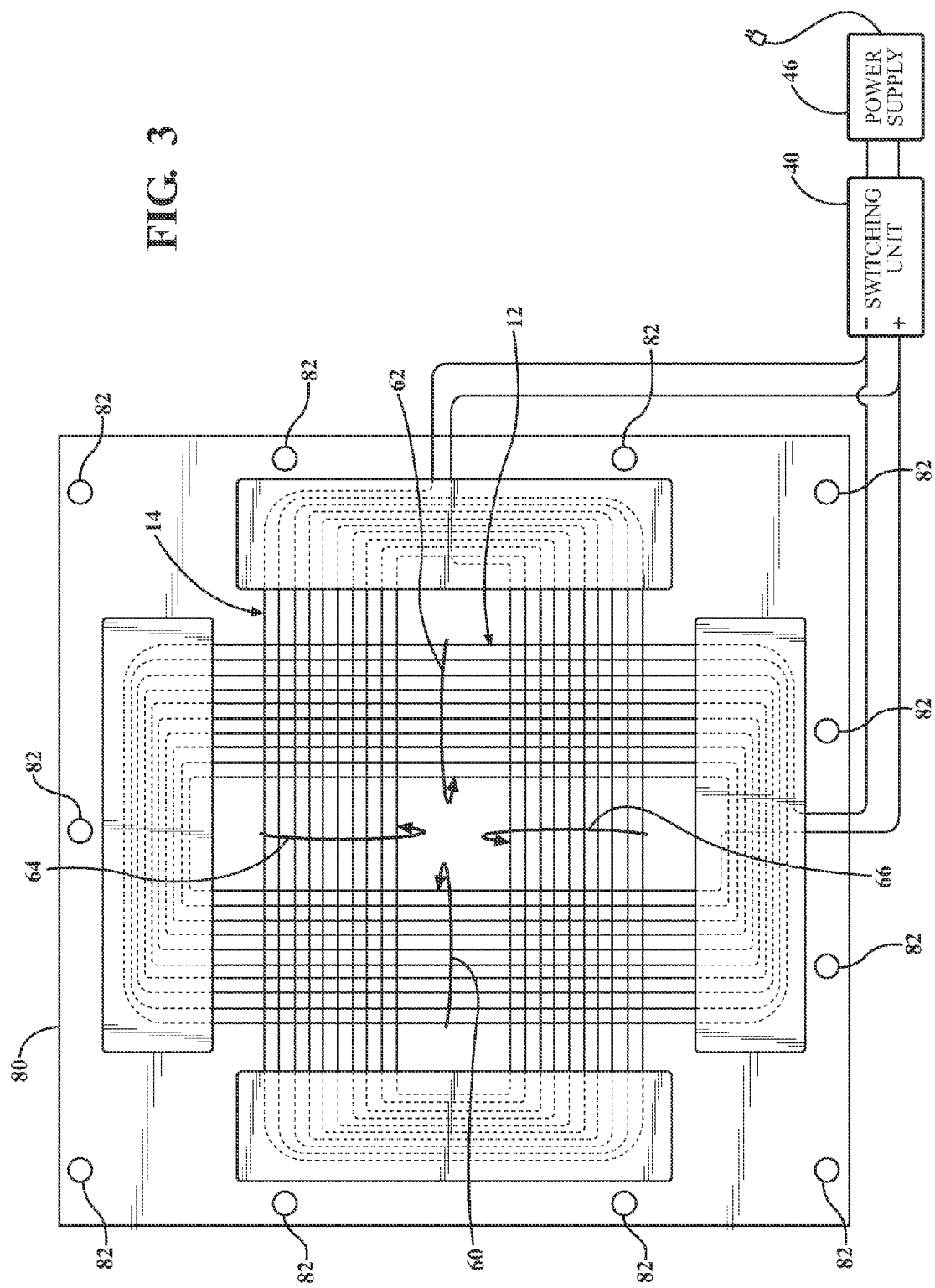
FIG. 3 depicts first and second coils embedded in a mat.

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Magnetic particle inspection (MPI) provides an indication of a flaw, such as irregularities or discontinuities, that may exist at or near the surface of a component, structure or other article fabricated from a ferromagnetic material. Referring to FIG. 1, a multidirectional magnetic particle inspection system 10 in accordance with the invention is shown. The system 10 includes first 12 and second 14 conducting coils located in a common plane. The first 12 and second 14 coils are each fabricated from a conductor such as copper wire or other suitable conductor.

The first coil 12 includes first 16 and second legs 18. The first coil 12 is shaped as a spiral having a plurality of spaced apart turns 128 beginning with a first innermost turn 24 and ending with a first outermost turn 26. The portions of each turn 128 located in the first leg 16 are substantially parallel to the portions of each turn 128 located in the second leg 18. The second coil 14 includes third 20 and fourth 22 legs. The second coil 14 is also shaped as a spiral having a plurality of spaced apart turns 130 beginning with a second innermost turn 32 and ending with a second outermost turn 34. The portions of each turn 130 located in the third leg 20 are substantially parallel to the portions of each turn 130 located in the fourth leg 22. The first 16 and second 18 legs are oriented substantially perpendicular to the third 20 and 22 fourth legs. In one embodiment, the turns 128, 130 have a rectangular shape, although it is understood that other shapes may be used. The first 24 and second 32 innermost turns of the first 12 and second 14 coils are connected by respective wires 36a, 36b to positive terminals 38a, 38b of a switching unit 40. In addition, the first 26 and second 34 outermost turns of the first 12 and second 14 coils are connected by respective wires 42a, 42b to negative terminals 44a, 44b of the switching unit 40.

The switching unit 40 may be a commercially available switching unit having a programmable relay, for example, that automatically switches the current flow to the first 12 and second 14 coils on and off. The switching unit 40 is connected to a power supply 46. The power supply 46 may be a commercially available alternating current (AC) power supply for providing AC current. Alternatively, the power supply 46 may be an alternating current (AC) power supply having a rectifier for supplying half wave rectified current.

In use, electric current is first supplied to either the first 12 or second 14 coil via the switching circuit 40. For purposes of illustration, the invention will be described with the current turned on first for the first coil 12 although it is understood that the current for the second coil 14 may be turned on first. Current flowing through the first coil 12 causes the generation of a circular magnetic field oriented about each of the turns of the first coil 12. Referring to FIG. 1A, an exemplary partial view of the first leg 16 of the first coil 12 is shown which depicts the first innermost turn 24 and subsequent second 48 and third 50 turns of the first coil 12. Current 52 flowing through the first coil 12 causes the generation of first 54, second 56 and third 58 circular magnetic fields about the first innermost 24, second 48 and third 50 turns, respectively. Referring to FIG. 1A in conjunction with FIG. 1, the first 54, second 56 and third 58 magnetic fields combine to form a first combined magnetic field 60 oriented perpendicular to the turns 128 in the first leg 16 wherein the magnetic field lines are in a first direction (as denoted by arrow). Circular magnetic fields are also generated about each turn 128 of the second leg 18 which then combine to form a second combined magnetic field 62 oriented perpendicular to the turns 128 in the second leg 18. Further, the second combined magnetic field 62 is in the same direction as the first combined magnetic field 60, i.e., in a direction perpendicular to the first leg 16 and second leg 18, to form a first overall magnetic field for the first coil 12.

Current to the first coil 12 is then turned off and current to the second coil 14 is turned on Current flowing through the second coil 14 causes the generation of circular magnetic fields about each turn of the third 20 and fourth 22 legs which combine to form third 64 and fourth 66 combined magnetic fields, respectively, each oriented perpendicular to the turns 130 of the third 20 and fourth 22 legs. Further, the third 64 and fourth 66 combined magnetic fields are also perpendicular to the first 60 and second 62 combined magnetic fields. The third 64 and fourth 66 combined magnetic fields combine to form a second overall magnetic field for the second coil 14. It is noted that strength of the first 60, second 62, third 64 and fourth 66 magnetic fields may be increased by increasing the number of turns 128,130 and/or the current 52 supplied to the first 12 and second 14 coils.

The area encompassed by the first 60, second 62, third 64 and fourth 66 magnetic fields forms an inspection zone 68 for inspecting an article. The system 10 also includes magnetic shields 70 fabricated from steel or other suitable shielding material located in respective end areas 72a, 72b of the first 12 and second 14 coils. The magnetic shields 70 shield undesirable magnetic fields generated by portions of the turns 128, 130 located in the end areas 72a, 72b to avoid interference with the magnetic fields in the inspection zone 68. Further, the spacing of the turns 128,130 relative to each other is decreased in the end areas 72a, 72b in order to minimize the size of the first 12 and second 14 coils.

FIG. 2 depicts a view of an exemplary turn 74 of the first coil 12 and an exemplary turn 75 of the second coil 14. Turns 74 and 75 are perpendicular to each other and both turns 74 and 75 are located underneath an article to be inspected such as a turbine blade 76 of a gas turbine. As previously described, current 52 to the first coil 12 is turned on resulting in the generation of an exemplary circular magnetic field 55 oriented perpendicular to the turn 74. The circular magnetic field 55 then magnetizes the blade 76 to enable detection of an exemplary flaw 78 oriented transverse to the orientation of the circular magnetic field 55. The current to the first coil 12 is then turned off and current 53 to the second coil 14 is subsequently turned on to generate an exemplary circular magnetic field 57 oriented perpendicular to turn 75 and circular magnetic field 55. This magnetizes the blade 76 to enable detection of a flaw 79 oriented transverse to the orientation of the circular magnetic field 57.

In one embodiment, the current provided to the first coil 12 by the power supply 46 has a different frequency than the current provided to the second coil 14 so as to generate a magnetic field in the first coil 12 having a different frequency than the frequency generated in the second coil 14. This reduces the effect of magnetization that may still exist in an article, after the current to a first coil is turned off, on subsequent magnetization of the article by a second coil.

Figure 4:
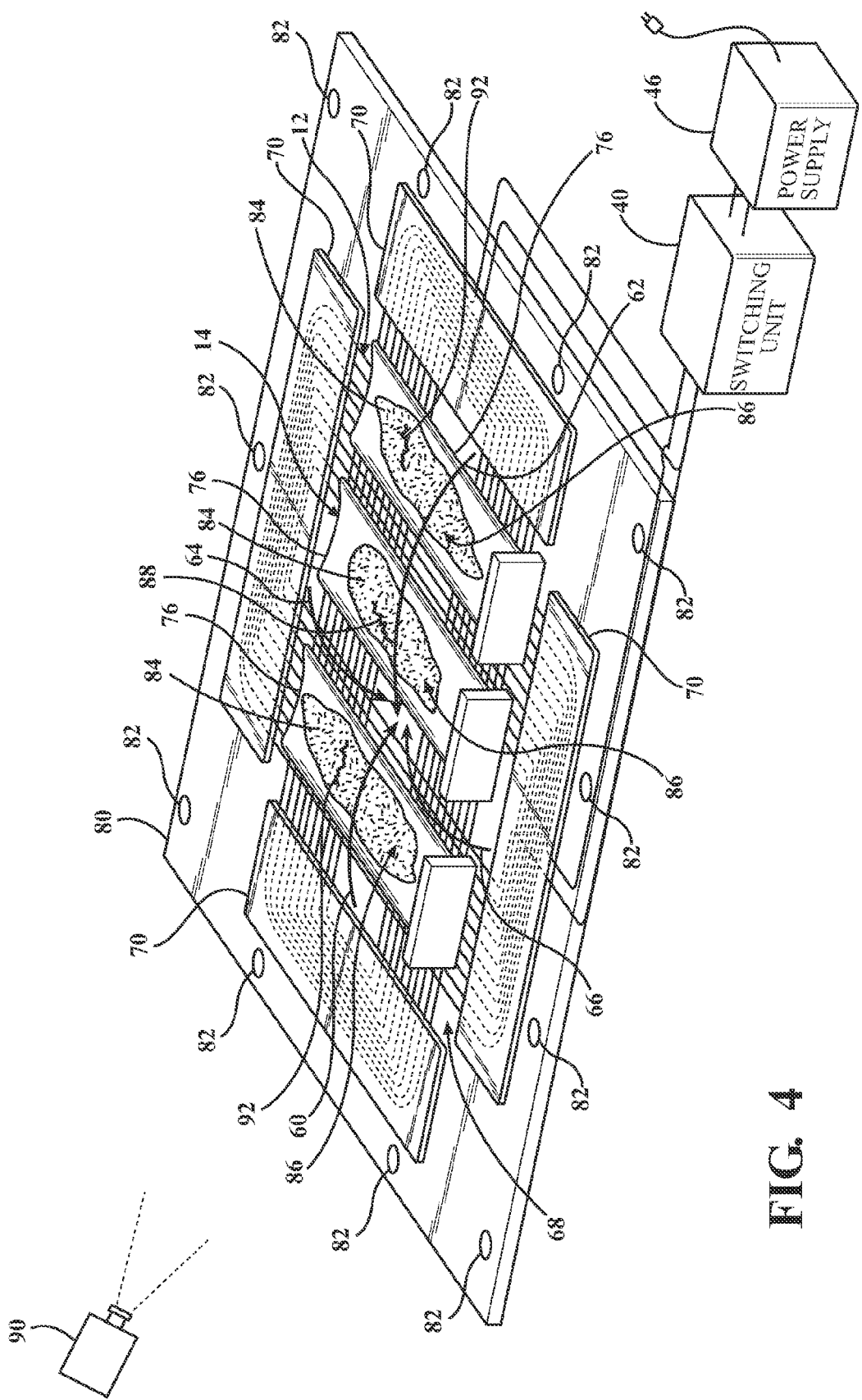
FIG. 4 depicts a plurality of turbine blades arranged on the mat for batch inspection.

In another embodiment, the first 12 and second 14 coils are embedded in a non-ferromagnetic material in order to protect the coils 12, 14 from damage. Referring to FIG. 3, the non-ferromagnetic material may be in the form of a flexible or rigid generally planar mat 80 fabricated from a polymer, aluminum alloy, titanium alloy or other suitable material. The mat 80 may include drainage holes 82 to enable drainage of the magnetic particle solution. Referring to FIG. 4, a plurality of blades 76 may be arranged on the mat 80 thus enabling batch inspection of the blades 76 and increasing productivity. Although blades 76 are shown in FIG. 4, it is understood that other types of articles may also be inspected by system 10. During an inspection procedure, the blades 76 are coated with a suitable magnetic particle solution 84 having a colored dye and magnetic particles 86, such as iron particles, suspended therein. The first coil 12 is then activated thus generating the first 60 and second 62 magnetic fields. The first 60 and second 62 magnetic fields cause the magnetic particles 86 in the solution 84 to collect at a flaw 88 oriented transverse to the orientation of the first 60 and second 62 magnetic fields. This enables observation of the flaw 88 by a user or recording by a camera 90, for example, while the first coil 12 is activated. The first coil 12 is then deactivated and the second coil 14 is activated thus generating the third 64 and fourth 66 magnetic fields which are perpendicular to the first 60 and second 62 magnetic fields. The third 64 and fourth 66 magnetic fields cause the magnetic particles 86 in the solution 84 to collect at flaws 92 oriented transverse to the orientation of the third 64 and fourth 66 magnetic fields. This also enables observation by the user or recording by the camera 90 as previously described.

The current invention may be used to inspect articles or components from power generation systems such as turbine blades from steam and gas turbines and blower blades for generators and other components. Further, the current invention may also be used to inspect other types of articles or components where high volume inspection is required such as in the automotive industry.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A magnetic particle inspection system, comprising:
    a first magnetizing coil oriented in a first direction, the first magnetizing coil configured as a rectangular spiral located in a plane;
    a second magnetizing coil oriented in a second direction perpendicular to the first orientation, the second magnetizing coil configured as a rectangular spiral located in a common plane with the first magnetizing coil;
    a mat for supporting an article to be inspected, wherein the first and second magnetizing coils are located in the mat;

a power supply for supplying power for energizing the first and second magnetizing coils; and a switching unit for switching current flow between the first and second magnetizing coils;

wherein the first magnetizing coil includes parallel first and second legs connected by opposing end areas of the first magnetizing coil and the second magnetizing coil includes parallel third and fourth legs connected by opposing end areas of the second magnetizing coil and oriented perpendicular to the first and second legs.

2. The system according to claim 1, wherein the first and second magnetizing coils form an inspection zone.

3. The system according to claim 2, further including magnetic shields for shielding the end areas of the first and second magnetizing coils from the inspection zone.

4. The system according to claim 1, wherein the first magnetizing coil is energized by current having a frequency which is different than a frequency of the current used to energize the second magnetizing coil.

5. The system according to claim 1, wherein the power supply provides half wave rectified power.

6. A magnetic particle inspection system for inspecting a plurality of articles, comprising:

a first magnetizing coil configured as a rectangular spiral located in a plane for generating a first magnetic field oriented in a first direction;

a second magnetizing coil configured as a rectangular spiral located in a plane for generating a second magnetic field oriented in a second direction perpendicular to the first direction, wherein the first and second magnetizing coils are located in a common plane;

a mat for supporting an article to be inspected and having a plurality of drainage holes, wherein the first and second magnetizing coils are located in the mat and the first and second magnetizing coils are sized to simultaneously inspect a plurality of articles;

a power supply for supplying power for energizing the first and second magnetizing coils; and a switching unit for switching current flow between the first and second magnetizing coils;

wherein the first magnetizing coil includes parallel first and second legs connected by opposing end areas of the first magnetizing coil and the second magnetizing coil includes parallel third and fourth legs connected by opposing end areas of the second magnetizing coil and oriented perpendicular to the first and second legs.

7. The system according to claim 6, wherein the first and second magnetizing coils form an inspection zone.

8. The system according to claim 7, further including magnetic shields for shielding the end areas of the first and second magnetizing coils from the inspection zone.

9. The system according to claim 6, wherein the first magnetizing coil is energized by current having a frequency which is different than a frequency of the current used to energize the second magnetizing coil.

10. The system according to claim 6, wherein the power supply provides half wave rectified power.

\* \* \* \* \*